United States Patent
Hancock et al.

(10) Patent No.: US 6,632,241 B1
(45) Date of Patent: Oct. 14, 2003

(54) SELF-EXPANDING, PSEUDO-BRAIDED INTRAVASCULAR DEVICE

(75) Inventors: David Hancock, San Francisco, CA (US); Peter S. Brown, Palo Alto, CA (US); Larry Voss, San Jose, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 0 days.

(21) Appl. No.: 09/532,261

(22) Filed: Mar. 22, 2000

(51) Int. Cl.[7] ................................................. A61F 2/06
(52) U.S. Cl. ...................................... 623/1.15; 128/898
(58) Field of Search ................................ 623/1.1–1.54; 128/898

(56) References Cited

U.S. PATENT DOCUMENTS

| | | |
|---|---|---|
| 4,733,665 A | 3/1988 | Palmaz |
| 4,856,516 A | 8/1989 | Hillstead |
| 5,015,253 A | 5/1991 | MacGregor |
| 5,061,275 A | 10/1991 | Wallsten et al. |
| 5,116,365 A | 5/1992 | Hillstead |
| 5,197,978 A | 3/1993 | Hess |
| 5,217,483 A | 6/1993 | Tower |
| 5,226,913 A | 7/1993 | Pinchuk |
| 5,314,472 A | 5/1994 | Fontaine |
| 5,476,508 A | 12/1995 | Amstrup |
| D380,266 S | 6/1997 | Boatman et al. |
| 5,643,339 A | 7/1997 | Kavteladze et al. |
| 5,718,159 A | 2/1998 | Thompson |
| 5,725,547 A | 3/1998 | Chuter |
| 5,755,775 A | 5/1998 | Trerotola et al. |
| 5,800,519 A | 9/1998 | Sandock |
| 5,843,168 A | 12/1998 | Dang |
| 5,876,432 A | 3/1999 | Lau et al. |
| 6,241,691 B1 * | 6/2001 | Ferrera et al. ............... 600/585 |

FOREIGN PATENT DOCUMENTS

| | | |
|---|---|---|
| EP | 0 737 452 A1 | 10/1996 |
| EP | 0 765 636 A2 | 4/1997 |
| EP | 0 820 726 A2 | 1/1998 |

* cited by examiner

Primary Examiner—Corrine McDermott
Assistant Examiner—Thomas Barrett
(74) Attorney, Agent, or Firm—Fulwider Patton Lee & Utecht, LLP

(57) ABSTRACT

A self-expanding, pseudo-braided device embodying a high expansion ratio and flexibility as well as comformability and improved radial force. The pseudo-braided device is particularly suited for advancement through and deployment within highly tortuous and very distal vasculature. Various forms of the pseudo-braided device are adapted for the repair of aneurysms and stenoses as well as for use in thrombectomies and embolic protection therapy.

17 Claims, 7 Drawing Sheets

SELF-EXPANDING, PSEUDO-BRAIDED INTRAVASCULAR DEVICE

BACKGROUND OF THE INVENTION

The present invention relates to self-expanding, knitted devices and more particularly, to a self-expanding knitted device for intravascular repair of distal and tortuous vasculature.

The vasculature of an animal or a human characteristically suffers from a variety of maladies. Vessel walls can weaken and become distended over time in response to blood flow and pressures, thereby resulting in formation of aneurysms. Such aneurysms can take on a myriad of forms. In particular, aneurysms may form at or near bifurcated vessels creating enlarged areas about the bifurcation, or may form a pocket, for example, in side walls of vessels. Due to the complications associated with aneurysms that rupture or otherwise fail, it is critical that an aneurysm be treated expeditiously and effectively. Intravascular treatment procedures include placing grafts within the aneurysm in a manner to ensure that blood flows through the graft rather than through the weakened vessel. Additionally, in the event that the aneurysm is in the form of a pocket in the side wall of a vessel, a stent might first be placed at the repair site then the pocket filled with material such as coils.

Stenoses also typically form in vasculature of humans and animals. Specifically, thrombotic or atherotic stenoses can form nearly anywhere in the vasculature. Such narrowing of the vessel is, of course, highly dangerous to the patient where the afflicted vessel provides the sole blood flow access to critical parts of the body. To treat such stenoses, a supporting structure can be placed at the diseased site for the purpose of enlarging and holding open the vessel. It is known in the art to employ stents for this purpose.

Vessel occlusions can also be treated by employing devices which are actuated to debulk and remove vessel occluding thrombi. This procedure is generally referred to as a thrombectomy. Typically, such devices are intravascularly advanced to the repair site and manipulated to remove the unwanted material from the vessel by physically engaging the thrombus and severing the same from the vessel wall.

Due to procedures such as thrombectomies or due to the natural, albeit undesirable, function of a patient's vasculature, emboli may be found traveling through a blood vessel. Embolic material can cause unwanted blockages or otherwise facilitate the formation of an occlusion in a vessel which too, can be highly dangerous to a patient. To address this problem, emboli-catching filters can be intravascularly placed within vasculature to thereby provide embolic protection. Such devices are often implanted temporarily within vasculature and removed upon being satisfied that the undesirable embolic material has been captured.

In certain situations, it is desirable to aid the formation of thrombus. For example, devices may be placed within aneurysmal spaces to slow and eventually cease blood flow therethrough. This procedure is sometimes referred to as embolic therapy, the basic thrust of which is to minimize or eliminate exposure of weakened sections of vasculature to blood flow and pressure.

Unfortunately, many areas of vasculature are inaccessible by a conventional intravascular repair means because the repair devices typically employed are often too large or rigid to be effectively advanced through tortuous vasculature or to vasculature that is very distal to the site through which the vasculature is accessed. Alternatively, in the event that there is success in advancing the repair devices to the diseased portion or repair site of the vasculature, conventional repair devices sometimes lack a large enough expansion ratio and/or radial stiffness to accomplish the necessary repair. Moreover, conventional devices can lack a profile suited to avoid traumatic engagement with a vessel wall or sufficient radiopacity so that remote observation is impossible.

Thus, where an intravascular approach is not available to the physician, invasive surgical techniques must be applied. To wit, a patient's chest, abdomen or cranium, for example, must be directly traversed in a major surgical procedure.

Hence, those concerned with repair of diseased vasculature have recognized the need for devices that can be employed to effectively repair distal and highly tortuous vasculature. The present invention fulfills these needs.

SUMMARY OF THE INVENTION

Briefly, and in general terms, the present invention provides devices contemplated for the repair of highly tortuous and distal vasculature. Basically, the invention is directed to a self-expanding, pseudo-braided structure that is characterized by having a large expansion ratio and high flexibility as well as an improved radial strength accomplished through the advantageous utilization of deflection energy.

In one preferred embodiment, the devices of the present invention are fabricated from a single filament configured into a repeating helical pattern that is interlaced into a mesh or pseudo-braided tubular shape. The filament may embody an elongate highly elastic and shape settable material. A reversal of direction that the filament undergoes presents a blunt, rounded surface that is atraumatic to vessel walls. The structure in the present application is referred to as pseudo-braided. Braiding is the interlacing of at least three wires at various angles to each other to form a braid, whereas the present invention uses a single filament that is interlaced with itself along the length of the structure at various angles. It is within the scope of the invention to interlace another filament or a plurality of other filaments into the pseudo-braid formed by the single filament.

In another aspect of the invention, the pseudo-braided or interlaced structure has a high expansion ratio with a low metal to space ratio. A large expansion ratio is accomplished by the unique single filament construction that provides additional springback forces.

In other aspects of the invention, there are various methods for terminating the filaments. Additionally, various methods are contemplated for adjusting the radiopacity as well as the expansion and spring characteristics of the pseudo-braided devices. Various methods are also contemplated for improving coverage of the pseudo-braided devices and enhancing the anchoring of the same within distal and tortuous vasculature.

The self-expanding, pseudo-braided devices disclosed are intended for use in addressing various maladies effecting vasculature. In particular, the self-expanding, pseudo-braided devices can be configured specifically to facilitate the repair of aneurysms and stenoses as well as to act as filter or thrombectomy devices.

These and other objects and advantages of the invention will become apparent from the following more detailed description, when taken in conjunction with the accompanying drawings of illustrative embodiments.

DESCRIPTION OF THE PREFERRED EMBODIMENTS

Figure 1:
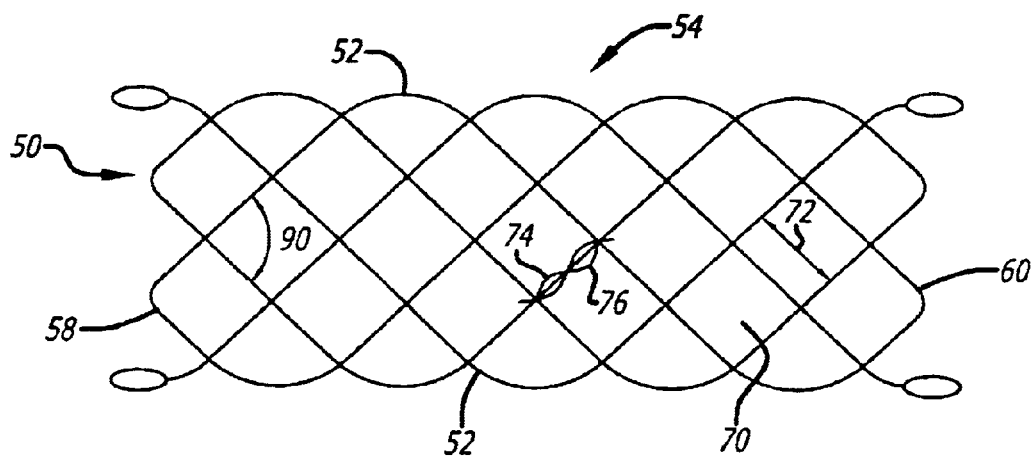
FIG. 1 is a side view of a pseudo-braided device of the present invention.
Figure 2:
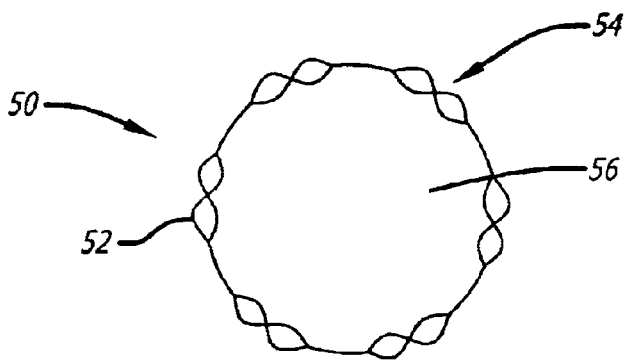
FIG. 2 is an end view of the pseudo-braided device shown in FIG. 1.

Turning now to the drawings, and particularly to FIGS. 1 and 2, there is shown a self-expanding pseudo-braided structure 50 of the present invention. The pseudo-braided device 50 is contemplated for use in highly tortuous and very distal vasculature of an animal or human. Due to its novel structure, the pseudo-braided device 50 is flexible in a compressed configuration and conformable to tortuous anatomy in a relaxed condition. Moreover, the device embodies high flexibility and a large expansion capability while providing sufficient radial force (i.e., hoop stiffness).

In a presently preferred embodiment, the pseudo-braided device 50 of the present invention is formed from the single filament 52. The filament 52 is configured into a repeating helical pattern that is interlaced upon itself by passing the end of the filament over then under the filament forming the helix as the end of the filament is wound down and back up the length of the structure to thereby form a generally tubular body 54. At the crossings of the filament there can be local deformations formed as the top wire is bent over the bottom wire however it has been discovered that for most applications deformations are not necessary to add spring force and resistance against fraying because of the ends formed by the reversal of winding. The tubular body 54 defines an interior lumen 56 and includes a first end 58 and second end 60.

Figure 3:
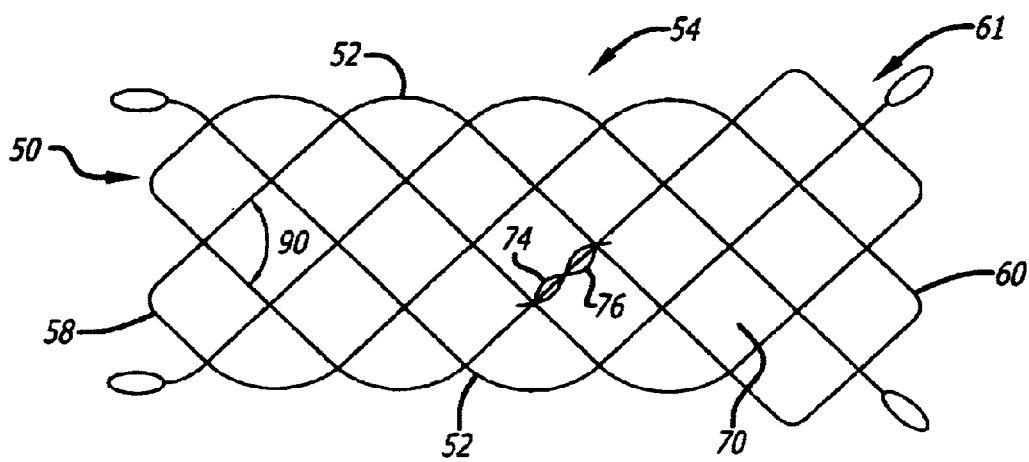
FIG. 3 is a side view of a pseudo-braided device of the present invention, depicting a device with a flared end.

It is also contemplated that the self-expanding pseudo-braided structure can embody modified tubular configurations. That is, as shown in FIG. 3, one end of the self-expanding pseudo-braided structure 50 can include an increased diameter section or flare 61. Alternatively, both ends of the device can include a flare 61, such flares can have the same general shape or one flare may be greater than the other.

The filament 52 is preferably an elongate, highly elastic and shape settable member. In one preferred embodiment, the filament 52 has a circular cross-sectional profile and can comprise nickel titanium alloy, eligiloy™, steel or other suitable materials.

In order to assemble the pseudo-braided device 50, it is contemplated that the filament 52 can be wrapped about a mandrel in a first direction and in a helical fashion for a desired length along the mandrel (not shown). Once the desired length is achieved, the direction of winding is reversed.

Figure 4:
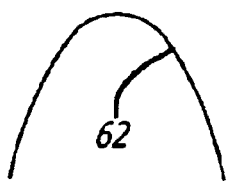
FIG. 4 depicts a first embodiment of a filament reversal.
Figure 5:
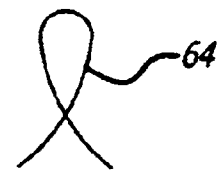
FIG. 5 depicts a second embodiment of a filament reversal.
Figure 6:
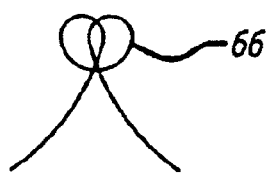
FIG. 6 depicts a third embodiment of a filament reversal.
Figure 7:
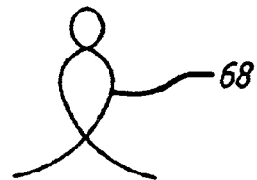
FIG. 7 depicts a fourth embodiment of a filament reversal.
Figure 8:
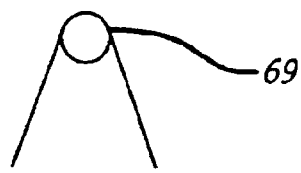
FIG. 8 depicts a fifth embodiment of a filament reversal.

Reversal of winding can be accomplished in a number of ways. It is contemplated, however, that the reversal of winding present a smooth, blunt surface that would be atraumatic to a vessel wall. As shown in FIG. 4, such an atraumatic reversal can be accomplished employing a simple arc 62. Atraumatic reversal can also be provided by single 64 or double 66 loop backs as well as a figure-8 reversal 68 or a full-turn helical reversal 69 as shown in FIGS. 5–8, respectively.

Various radii of curvature and length of loops can be employed according to the application. The loops or hoops of the various reversals contemplated can have a constant or irregular radii of curvature and the loops can have an acute radius of curvature (not shown). It is believed that minimizing stress concentrations in the reversals may have the added benefit of optimizing springback forces. Thus, stress concentration in the reversals can also be varied for a particular application. Moreover, in order to facilitate the reversal of direction of the filament 52, the mandrel can have pegs extending therefrom at desired intervals, about which the filament can be routed.

Once a reversal direction is made, the filament is interlaced in an over/under fashion about itself in a helical pattern in the reverse axial direction but same rotational direction. The desired density of the wall 70 defining the tubular body 54 is accomplished by altering the number of reversals and the longitudinal spacing 72 of adjacent members wrapped in the helical pattern. That is, the number of traversals, which is defined as the portion of the filament 52 between two reversals of direction, can be varied as can the number of revolutions per traversal. Typically, the number of reversals at each end 58, 60 of the tubular body 70 number from six (6) to twelve (12) and as much as twenty (20).

Upon achieving a desired pseudo-braided pattern and wall density, the ends 74, 76 of the filament 52 are joined. There are a myriad of ways in which the ends 74, 76 can be joined. While the figures illustrate such joining as occurring generally at the middle of the pseudo-braided device 50, it is also contemplated that such joining can occur at the ends of the structure or anywhere in between. Ultimately, however, it is desired that the joining of the ends 74, 76 of the filament 52 be accomplished in a manner such that the vessel wall is presented with as atraumatic a surface as necessary for a particular application, there is a low profile, and no compromise in device function.

Figure 9:
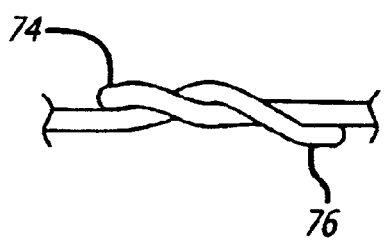
FIG. 9 depicts a first embodiment of a method for joining ends of a filament.
Figure 10:
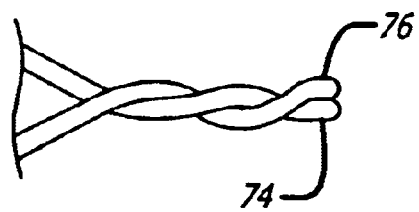
FIG. 10 depicts a second embodiment of a method for joining ends of a filament.
Figure 11:
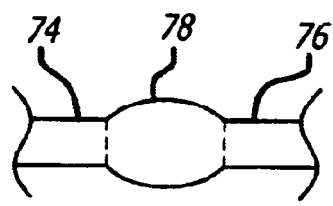
FIG. 11 depicts a third embodiment of a method for joining ends of a filament.

As shown in FIGS. 9 and 10, one way of joining the end 74, 76 of the filament 52 is to twine them together. The ends 74, 76 of the filament can also be joined by soldering or welding to form a welded joint 78 as shown in FIG. 11. A preferred method of welding is laser welding.

Figure 12:
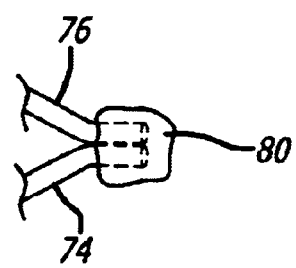
FIG. 12 depicts a fourth embodiment of a method for joining ends of a filament.

Alternatively, the ends 74, 76 of the filament 52 can be joined utilizing potted tantalum powder 80, as depicted in FIG. 12. In order to do so, the tantalum powder is first mixed with an epoxy. Thereafter, the filament 50 is coated with the tantalum/epoxy compound and left to cure.

Figure 13:
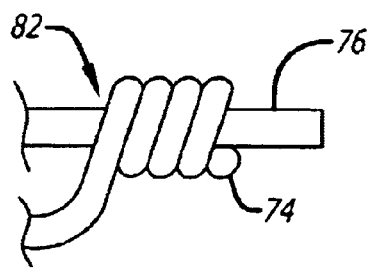
FIG. 13 depicts a fifth embodiment of a method for joining ends of a filament.

Moreover, the ends 74, 76 of the filament 52 can be configured into a linear slide arrangement 82 (see FIG. 13). In such an arrangement, one filament end 74 is wrapped around the other filament end 76 which remains straight or undeformed. This means for joining the end 74, 76 of the filaments 52 has the advantage of compensating for length mismatches. To wit, one wire can move relative to the other.

Figure 14:
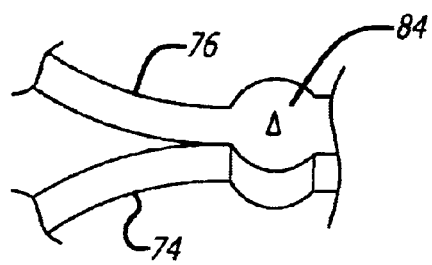
FIG. 14 depicts a sixth embodiment of a method for joining ends of a filament.

The ends 74, 76 of the filament can also be formed with flattened welding surfaces 84 (FIG. 14). These weld surfaces 84 are then aligned and thereafter welded together by conventional methods.

Figure 15:
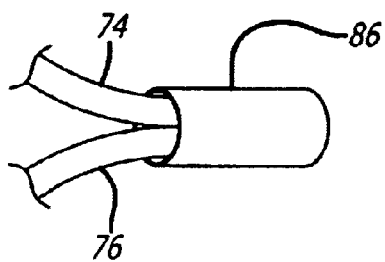
FIG. 15 depicts a seventh embodiment of a method for joining ends of a filament.
Figure 16:
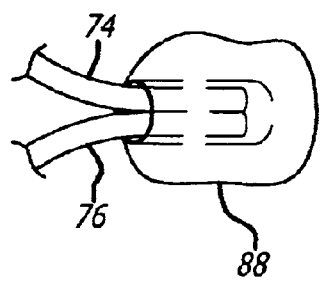
FIG. 16 depicts a eighth embodiment of a method for joining ends of a filament.

Finally, the ends 74, 76 of the filament 52 can be crimped together using a sleeve 86 or are otherwise joined by way of a ball member 88 (FIGS. 15 and 16). In both instances, a bore is provided to receive both ends 74, 76 of the filament 52. In the case of the sleeve 86 embodiment, the outer surface of the sleeve 86 can be crimped to retain the sleeve 86 on the ends 74, 76 of the filament 52. A press fit is contemplated for the ball 88 and configuration.

The assembled pseudo-braided device 50 embodies a number of unique features. In particular, the reversal of the knit direction provides a resilient response at the ends 58, 60 of the pseudo-braided device 50 compared to that of other conventional braided structures that have unconnected wire ends. That is, reversals of direction act as a spring and tend to attempt to return to pseudo-braided device to its original expanded shape. This feature allows the pseudo-braided device 50 to be compressed to smaller than ten (10) percent of its original diameter and once released, to spring back to its original uncompressed configuration. Accordingly, the pseudo-braided device 50 of the present invention is characterized by having a very large expansion ratio.

Embodying a very large expansion ratio provides the pseudo-braided device 50 of the present invention with a number of advantages. In particular, the pseudo-braided device 50 can be delivered within vasculature using very small diameter catheters or microcatheters. This in turn allows for the placement of the pseudo-braided device 50 within very distal vasculature. Thus, using microcatheters to deliver the pseudo-braided device 50 facilitates advancement through highly tortuous as well as very narrow vessels such as in the cerebral vasculature.

Furthermore, the reversals of direction of the filament 50 tend to improve radial force (i.e., hoop stiffness) by forcing deflection energy to bend the reversal arc as well as displace the same. With particular reference to FIG. 4, reversals defined by simple bends 62 embody relatively high stress concentrations at the bend 62. Such high stress concentrations may be suitable for a purpose requiring a particular deflection energy. In contrast, reversals defined by full-turn helixes (FIG. 8), for example, tend to distribute stress concentrations throughout the helix 69 and therefore provide a different deflection energy. By comparison, braided devices that lack reversals deflect in response to a load much more readily than the ends 58, 60 of the pseudo-braided device of the present invention and those braided devices only rely on pivots at the crossings of the wires whereas the present invention embodies crossings plus spring ends.

The crossing angle 90 can also be varied for a particular application. The crossing angle 90 is defined by two portions of the filament that cross each other. It is presently contemplated that the crossing angle can range up to approximately 90 degrees or more. It has been found that the braid angle directly affects radial stiffness and conformability which can thus be optimized for a particular application.

It has also been recognized that joining the ends 74, 76 of the filament maintains filament alignment. Filament alignment is important particularly when deploying the pseudo-braided device 50 in extremely tortuous vessels for a number of reasons. First, in the event the filaments 52 were permitted to slide out of place, weaker areas would be created in the pseudo-braided device 50. Those weaker areas would have an increased propensity to buckle. Secondly, if filaments 52 were to slide out of place, the mesh openings can become variable. As a result, there would be larger openings in the mesh or interlaced structure in some places that would reduce functionality of the device. Finally, if filaments were permitted to slide out of place, catheter distortion during deployment will likely increase. Thus, when the filaments 52 of the pseudo-braided device maintain good alignment while in the compressed condition, the individual radial forces of each filament 52 add together to form a consistent radial force in all directions along the length of the pseudo-braided device 50.

It is also possible to produce a pseudo-braided device 50 that is comprised of one wire, where that one wire has variations along its length that corresponds to specific pseudo-braiding processes of a particular desired configuration. To wit, a wire could be masked and chemically etched to produce a variable diameter wire that corresponds to the pseudo-braided device 50 design of choice, such that for example, the bends of the filament 52 that comprise the ends of the pseudo-braided device 50 can be of a smaller diameter than the wire that comprises the remainder of the pseudo-braided device body 70. Additionally, the bends could be of a larger diameter for providing a greater expansion rate and radial force. These variations may advantageously create a pseudo-braided device 50 with a desired strength, without increasing its resistance to being pushed through a catheter lumen in a compressed configuration.

This kind of design variation could be followed for other attributes as well. For example, such as for non-thrombogenic coatings, coatings laced with therapeutic drugs, plating processes to selectively increase radiopacity, and plating processes to selectively increase stiffness.

Alternatively, rather than a round profile, the filament 52 can be formed from a filament having various other cross-sectional profiles. That is, the filament can comprise an oval, triangular, rectangular, square, bowed, crescent moon, or tapered profiles. The filament 52 itself can also be formed from a small diameter tube or be configured into a coil along its length.

It is also recognized that the desired pseudo-braided structure can be made from a plurality of filaments 52. Such plurality of filaments 52 can be configured with a number of reversals of varying types, so that the benefits associated therewith can be used advantageously. The ends of these filaments can also be joined together to provide atraumatic engagement with vessel walls as discussed above.

When deploying the pseudo-braided device 50 of the present invention within a patient's vasculature, it is desirable to be able to remotely observe the placement thereof. Thus, it is important that the pseudo-braided device 50 be sufficiently radiopaque so that such remote observation is possible by conventional methods such as fluoroscopy.

Referring now to FIGS. 15 and 16, the radiopacity of the pseudo-braided device 50 can be enhanced by employing platinum or other sufficiently radiopaque materials as the crimping sleeve 86 or the ball end 88. Platinum coils (not shown) could similarly be wrapped about portions of the filament 52 to act as radiopaque markers. Additionally, the filament 52 can be twined with one or more platinum filaments along its length, thereby providing a pseudo-braided device 50 that is radiopaque from one end to the other.

Additionally, it is contemplated that in certain applications, it may be desirable to plate the filament with gold or platinum. The entirety of the tubular body 70 can be plated or the reversals could be masked and the remainder of the body 70 be plated. By thus masking the reversals, the desirable spring characteristics of the pseudo-braided device 50 of the present invention can be preserved.

Figure 17:
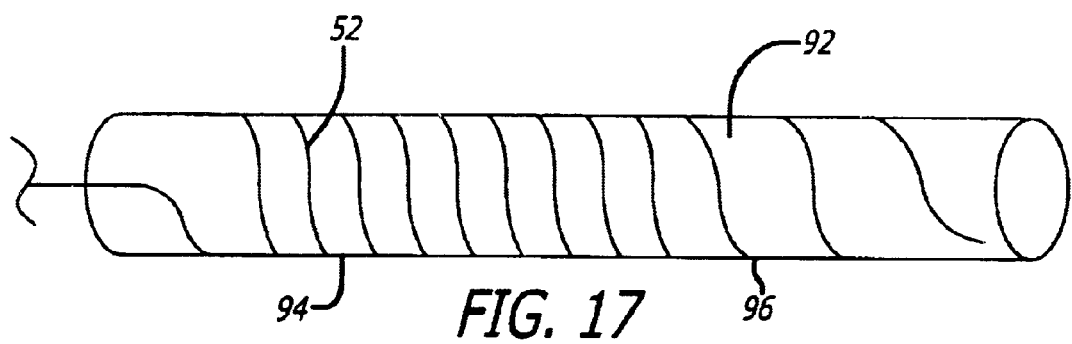
FIG. 17 is a perspective view of a first alternative method of forming a pseudo-braided device of the present invention.
Figure 18:
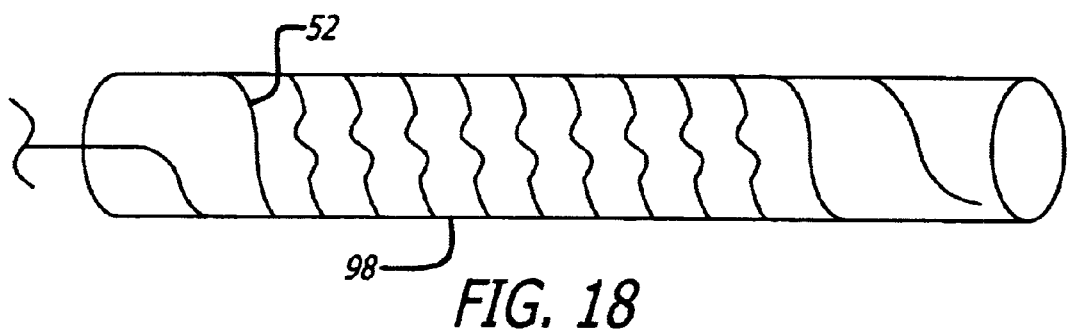
FIG. 18 is a perspective view of a second alternative method of forming a pseudo-braided device of the present invention.

Referring now to FIGS. 17 and 18, there is shown methods of manufacturing the pseudo-braided device 50 of the present invention in a manner to optimize vessel coverage for particular applications. As shown in FIG. 17, a particular configuration of the pseudo-braided device 50 can be formed by wrapping a filament 52 about a forming mandrel 92 such that there is tight winding at an inferior end portion 94 and relatively looser winding at a superior end portion 96. The tightly wound portion being contemplated to provide the resultant pseudo-braided device 50 with structure for anchoring and for increasing surface area for vessel coverage. The more loosely wound portion provides a gradual transition to the more tightly wound portion as well as a means for more easily deploying the pseudo-braided device 50 when it is released from a catheter.

FIG. 18 additionally depicts a wavy midsection 98 which is contemplated for use in also increasing coverage when the pseudo-braided device is deployed within a vessel. The waves can generally resemble a sinusoidal path and can also take on an undulating serpentine pattern. Such waves 98 can alternatively extend the length of the filament thereby providing the pseudo-braided device with increased coverage throughout its length. Such waveforms are created by threading the filament through a mesh setting shape then again wrapping the filament about a mandrel again setting the shape.

It has also been recognized that the waveforms like those shown in FIG. 18 can be spanned with a highly elastic material for the purpose of again improving coverage. As with the closely wound filament embodiment, the waves can additionally improve anchoring capabilities by enhancing in a circumferential direction, the traction between the vessel wall and the pseudo-braided device 50.

Figure 19:
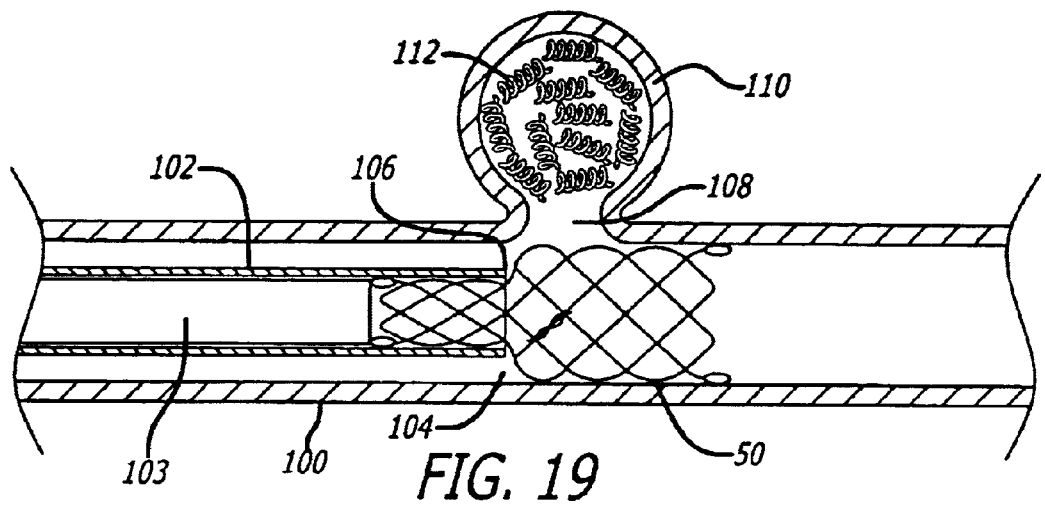
FIG. 19 is a side view of a sectioned portion of a blood vessel suffering from an aneurysm and a pseudo-braided device of the present invention being deployed from a catheter.
Figure 20:
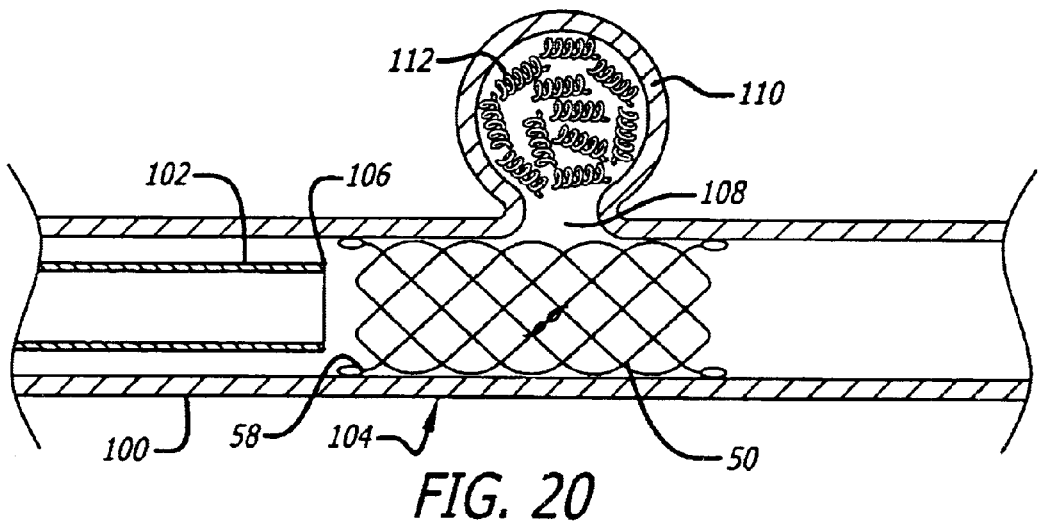
FIG. 20 depicts the implantation of the device of FIG. 19 within a vessel.

The pseudo-braided device 50 of the present invention has applications in a number of areas including operating as an aneurysm cover, in conjunction with thrombotic and artherotic stenosis therapy, as an embolic protector, as a thrombectomy device and in embolic therapy. As stated, due to its high expansion ratio and superior flexibility, the pseudo-braided device 50 can be placed within vasculature and advanced deep within the patient's anatomy to a repair site. Once there, the pseudo-braided device 50 can be deployed within highly tortuous vascular for the purpose of addressing the particular malady effecting the vessel. As shown in FIGS. 19 and 20, the pseudo-braided device 50 of the present invention can be advanced within a blood vessel 100 using a delivery catheter 102. Due to the ability to reduce the pseudo-braided device 50 to less than 10 percent of the expanded diameter, microcatheters can be utilized for this purpose. In a preferred embodiment, the delivery catheter is contemplated to include or cooperate with a pusher 103 that operates to facilitate relative movement between the pseudo-braided device 50 and the delivery catheter 102.

Figure 21:
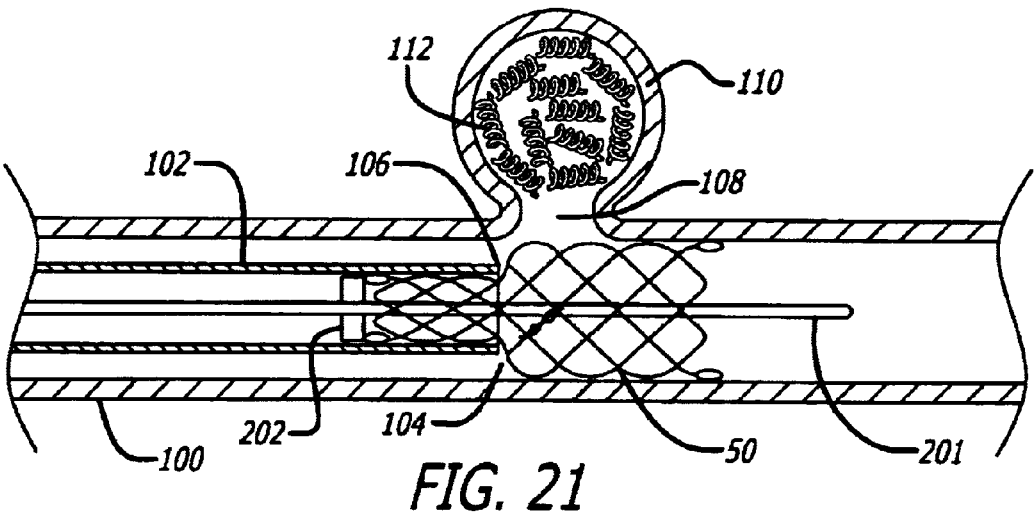
FIG. 21 is a side view of a sectioned portion of a blood vessel suffering from an aneurysm and a pseudo-braided device of the present invention being deployed from an alternative embodiment of a delivery catheter.

In an alternate configuration (See FIG. 21), a compressed stent has a lumen that a standard guidewire 201 can freely pass through. This allows improved access. When ready, the guidewire 201 can be withdrawn and replaced with the push wire 200 or the guidewire 201 can have a proximally placed pushing ring 202 that accomplishes the ejection of the pseudo-braided device from the delivery catheter 102.

Upon advancing the delivery catheter 102 to a repair site 104, the pseudo-braided device is deployed from a distal end 106 of the delivery catheter 102 (FIG. 20). It is contemplated that any number of conventional means may be employed to eject the pseudo-braided device from the delivery catheter 102, including but not limited to a pusher device (not shown) configured coaxially within the delivery catheter 102 which operates to engage a proximal end 58 of the pseudo-braided device 50 while withdrawing the delivery catheter 102 proximally.

As stated, the pseudo-braided device 50 of the present invention is also particularly suited to operate as an aneurysm cover. As shown in the figures, the pseudo-braided device 50 can be deployed to overlay an opening 108 to an aneurysm 110 formed in a sidewall of a vessel. By being so positioned, the pseudo-braided device 50 can redirect flow from entering the aneurysm, become covered with endothelium cells and seal off the opening into the aneurysm, or retain embolic coils 112 or other thrombus producing materials inserted in the aneurysm sack 110. It is to be noted that it is preferred to implace the pseudo-braided device 50 prior to embolic material as the same prevents prolapse of material into the parent vessel.

Figure 22:
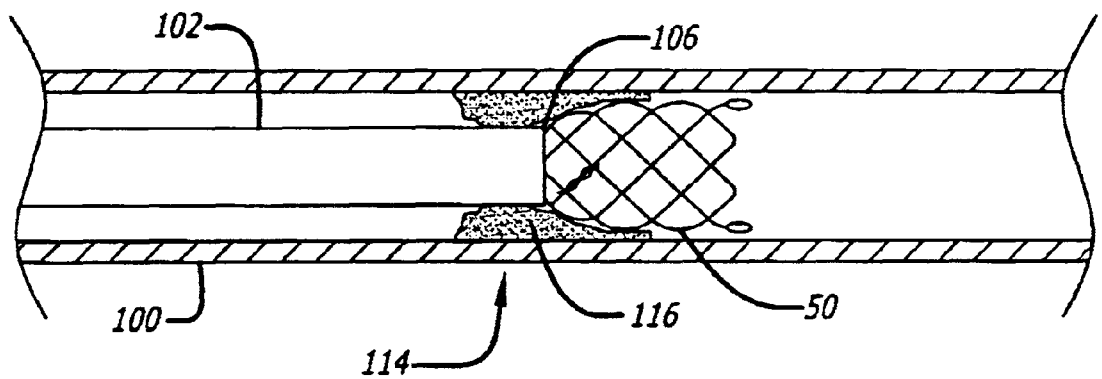
FIG. 22 is a side view of a sectioned portion of a blood vessel suffering from a stenosis and a pseudo-braided device of the present invention being deployed from a catheter.
Figure 23:
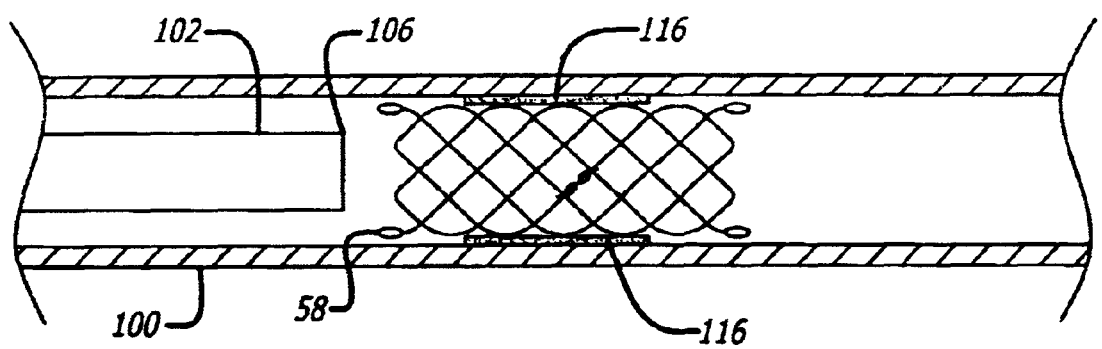
FIG. 23 depicts the implantation of the pseudo-braided device of FIG. 22 within a vessel.

Using similar methods, the pseudo-braided device 50 of the present invention could additionally be employed to repair thrombotic or artherotic stenoses 14 found in a blood vessel 100 (See FIGS. 22 and 23). Due to its high expansion ratio and enhanced radial strength (i.e., hoop strength), the pseudo-braided device 50 can be deployed across the stenosis 114 and be allowed to self-expand to thereby press the thrombotic or artherotic material forming the stenoses against the walls of the vessel 100. By doing so, the pseudo-braided device operates to hold open and enlarge the vessel 100 at the repair site.

Figure 24:
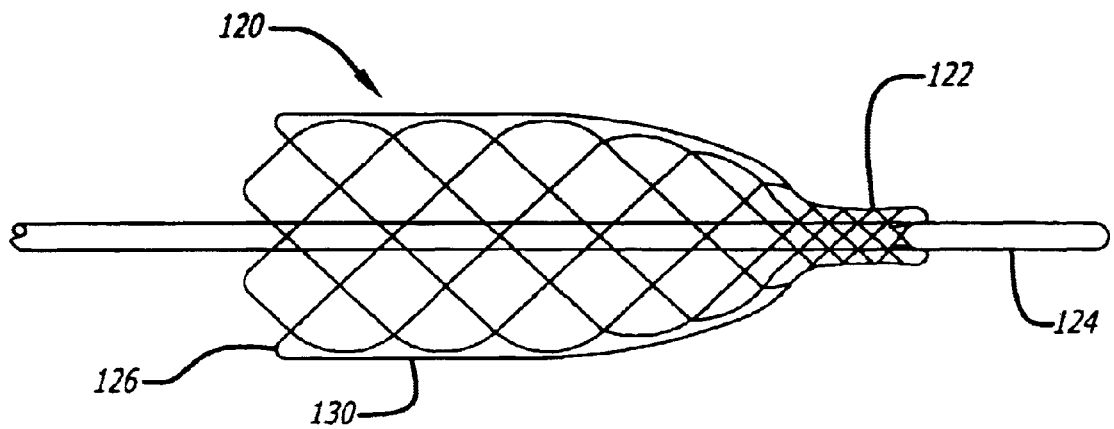
FIG. 24 is a side view of a pseudo-braided device of the present invention configured as an embolic protection device.
Figure 25:
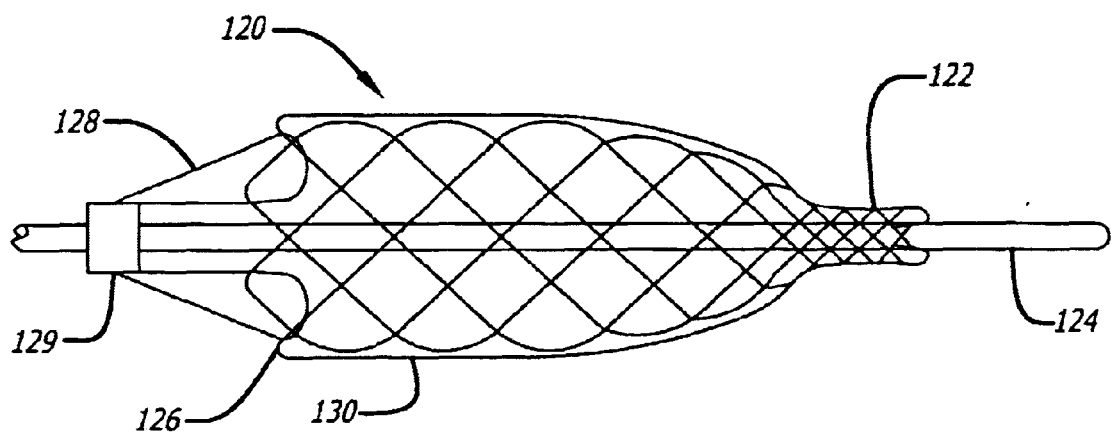
FIG. 25 depicts a side view of an alternate embodiment of the pseudo-braided device of the present invention configured as an embolic protection device.

By reconfiguring the basic structure of the pseudo-braided device 50, as previously mentioned, the advantages provided by the present invention can be used to address other maladies effecting vessels. More specifically, the pseudo-braided device 50 can be reconfigured as an embolic protection device 120. With reference to FIGS. 24 and 25, a superior end portion 122 of the contemplated embolic protection devices can be necked down so as to form a generally conical profile. Such necking could be accomplished by way of altering the manufacturing process or the superior end 122 of the pseudo-braided structure can simply be restrained to a relatively smaller cross-sectional profile by way of adhesion or mechanical devices. It is contemplated that the superior end 122 of the embolic protection device 120 be affixed by conventional means to an elongate member 124 that is positionable within a delivery catheter similar to that depicted in FIGS. 19–23. The inferior end 126 of the embolic protection device 120, in its expanded form, provides a generally circular, cross-sectional profile, opening for receiving blood flow.

In one embodiment of the embolic protection device 120 (FIG. 25), a plurality of proximally extending filaments or wire loops 128 are routed about portions of the filament defining the inferior end 126 of the embolic protection device 120. Proximal ends 129 of the loops can be affixed to a collar that is intended to slide along the elongate member 124. Independent control of the collar is also contemplated such that a separate actuator (not shown) which extends to the operator can be supplied to manipulate the position of the collar along the elongate member 124. In either case, the loops 128 are provided in the event additional control of the opening and closing of the embolic protection device 120 is desired.

Upon advancing the embolic protection device 122 to a desirable location within a patient's vasculature, the elongate member 124 is held stationary while the delivery catheter (not shown) is withdrawn proximally. The inferior end portion 26 and a tubular midsection 130 of the embolic protection device 122 are then permitted to self-expand against the walls of the vessel into which the device is deployed. The fully opened embolic protection device 120 permits blood to flow into its interior and through its pseudo-braided walls but acts as a barrier to emboli passing through the blood. That is, emboli entering the embolic protection device 120 are captured by its pseudo-braided structure. The captured emboli can thereafter be removed from the patient's vasculature when the embolic protection device 120 is removed or other conventional means such as suction devices can be employed to remove the emboli.

Figure 26:
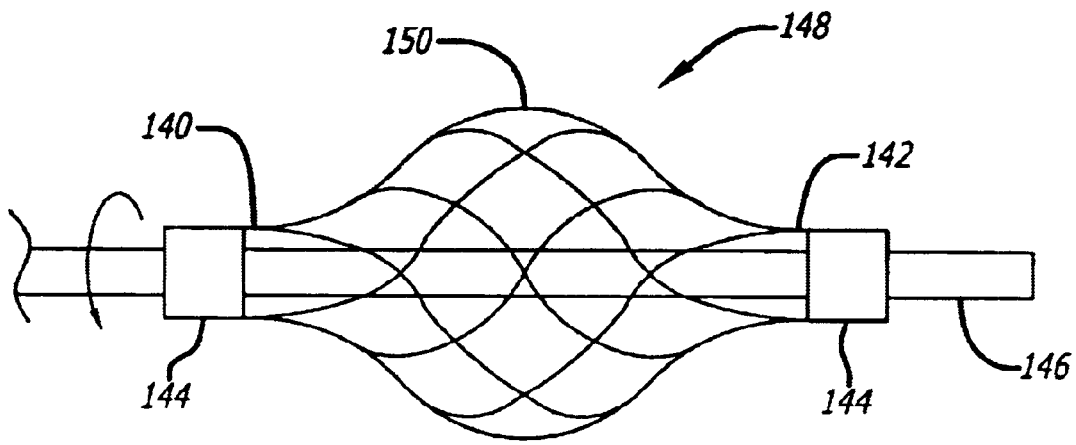
FIG. 26 is a side view of a pseudo-braided device of the present invention configured as a thrombectomy device.
Figure 27:
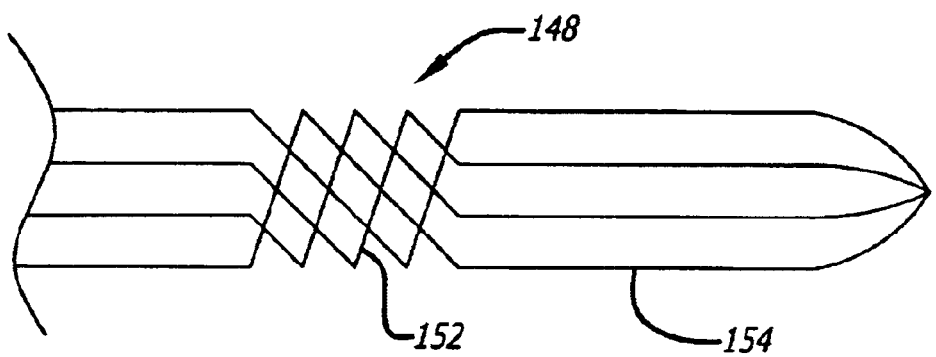
FIG. 27 depicts a side view of an alternate embodiment of the pseudo-braided device of the present invention configured as a thrombectomy device.
Figure 28:
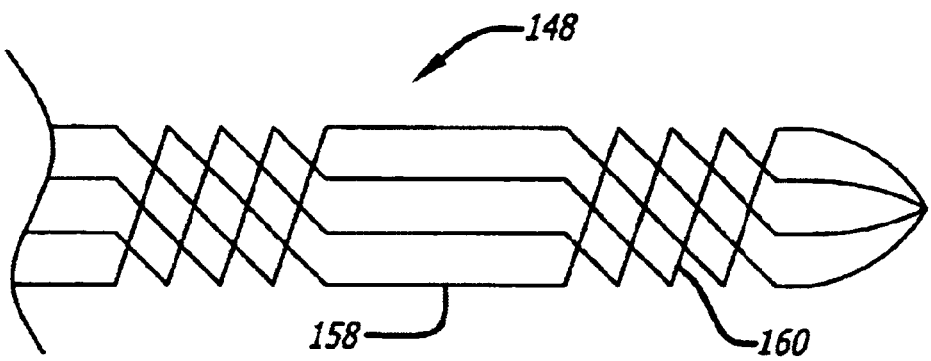
FIG. 28 depicts a side view of yet another embodiment of the pseudo-braided device of the present invention configured as a thrombectomy device.

Turning now to FIGS. 26–28, there are shown various embodiments of the present invention configured as thrombectomy devices 148. Such thrombectomy devices 148 can be advanced and deployed within a patient's vasculature using the delivery catheter depicted in FIGS. 19–23. With specific reference to FIG. 26, the pseudo-braided device of the present invention can be attached at its ends 140, 142 by way of collars 144 to an elongate member 146 to thereby form one embodiment of a thrombectomy device 148. Upon deployment and expansion within a target vessel, the thrombectomy device assembly 148 provides a mid-section 150 that is well-suited for engaging and, upon rotation of the device, shearing thrombus from a vessel wall. In order to facilitate self-expansion, one collar 144 is permitted to slide along the elongate member 146, while the other collar is longitudinally fixed thereto.

As shown in FIGS. 27 and 28, the thrombectomy devices 148 may also embody pseudo-braided portions of varied density. For example, the more densely pseudo-braided midsection 152 of the device depicted in FIG. 27 is particularly suited for accomplishing the thrombectomy whereas its less densely pseudo-braided superior end portion 154 is intended for capture of emboli. The thrombectomy device 148 of FIG. 28 embodies a less densely pseudo-braided midsection contemplated for macerating a thrombus adhering to a blood vessel wall whereas its superior end portion 160, being more densely pseudo-braided, is configured for removal and capture of emboli.

Figure 29:
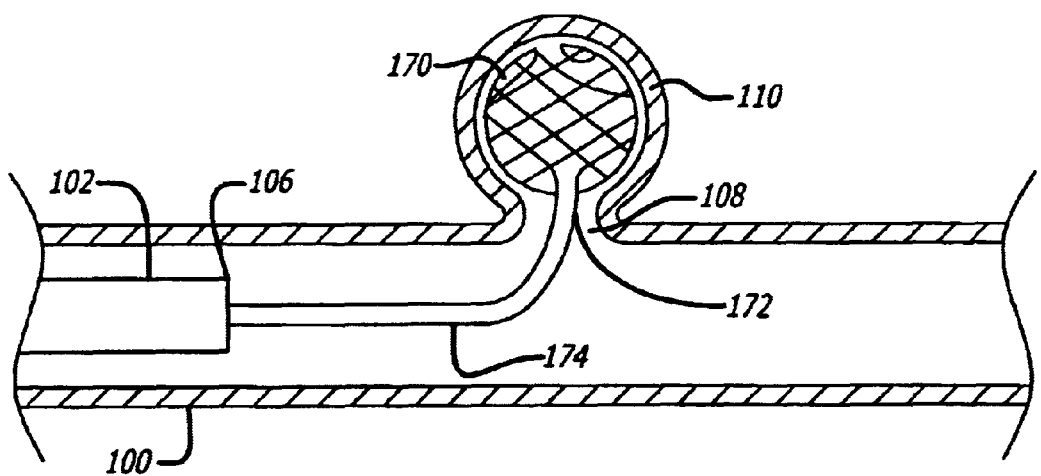
FIG. 29 is a side view of a sectional portion of a portion of a blood vessel suffering from an aneurysm and a pseudo-braided device of the present invention configured to be placed within the aneurysm.

The pseudo-braided device 50 of the present invention can also be closed at each of its ends to form an expandable spherical shape that is suited as an embolic therapy device 170. With reference to FIG. 29, such an embolic therapy device can be advanced within a vessel using a delivery catheter 102. The embolic therapy device 170 can then be deployed within an aneurysm sack 110 and permitted to self-expand to thereby facilitate thrombus formation. A conventional releasable connection 172 to an elongate delivery assembly sub-component 174 is contemplated so that the embolic therapy device 170 can remain in the aneurysm 110 when the delivery assembly is removed from the patient.

In view of the foregoing, it is clear that the pseudo-braided device of the present invention is useful in numerous of applications. Moreover, due to its high expansion ratio and flexibility, the pseudo-braided device of the present invention can be employed to repair very distal as well as tortuous portions of a patient's vasculature.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A method involving employing a device for use in embolic therapy within vasculature having an aneurysm sac, comprising:

gaining access to vasculature;

placing within an aneurysm sac a device including an elongate filament configured into a pseudo-braided pattern and formed to define a generally tubular body with a first end and a second end; and configuring the body to facilitate thrombus formation within the aneurysm sac, said first and second ends each being defined by a plurality of endless reversals of direction of said filament.

2. The method of claim 1, the device further comprising at least one more elongate filament interlaced in the pseudo-braided pattern.

3. The method of claim 1, wherein at least one of said plurality of reversals embody loops having a variable radius of curvature.

4. The method of claim 1, wherein said pseudo-braided pattern is uniform along a length of said tubular body.

5. The method of claim 1, wherein said pseudo-braided pattern is non-uniform along a length of said tubular body.

6. The method of claim 1, wherein said filament is undulated between crossing points.

7. The method of claim 1, wherein said filament includes a first end and a second end of said filament, said first and second ends being joined together by epoxy.

8. The method of claim 1, wherein said filament includes a first end and a second end of said filament, said first and second ends being joined in a middle portion of the device.

9. The method of claim 1, wherein said filament includes a first end and a second end of said filament, said first and second ends being joined at an end of the device.

10. The method of claim 1, wherein said filament is made from a tube.

11. The method of claim 1, wherein said filament has a variable cross-sectional profile.

12. The method of claim 1, wherein said plurality of endless reversals of direction function to enhance hoop strength of said device at said first and second ends thereof.

13. The method of claim 1, wherein said device can be reduced to less than 10 percent of its expanded diameter.

14. The method of claim 1, wherein said device can be delivered into a patient's vasculature by a microcatheter.

15. The method of claim 1, wherein said device is self-expanding.

16. A method involving employing a device for use in embolic therapy within vasculature having an aneurysm sac, comprising:

gaining access to vasculature;

placing a device including an elongate filament configured into a pseudo-braided pattern and formed to define a generally spherical body within a delivery microcatheter, said generally spherical body formed by a generally tubular body having first and second ends that are collapsed upon themselves, said first and second ends each comprising a plurality of endless reversals of direction of said filament the spherical body shaped to facilitate thrombus formation within the aneurysm sac, the delivery microcatheter releasably connected to said spherical body;

placing the delivery microcatheter within vasculature; and deploying the device to facilitate thrombus formation within an aneurysm sac.

17. The device of claim 16, wherein said spherical body is self-expanding.

\* \* \* \* \*